United States Patent [19]

Filipi et al.

[11] 4,313,906
[45] Feb. 2, 1982

[54] TWO DIMENSIONAL TWO PHASE THIN LAYER CHROMATOGRAPHY PLATE AND METHOD

[75] Inventors: Thomas J. Filipi, Parsippany; Michael E. Mazzei, Butler, both of N.J.

[73] Assignee: Whatman, Inc., Clifton, N.J.

[21] Appl. No.: 67,424

[22] Filed: Aug. 17, 1979

[51] Int. Cl.³ .................................. G01N 31/08
[52] U.S. Cl. ............................ 422/69; 23/230 R; 23/230 B; 210/198.3; 422/70; 73/61.1 C
[58] Field of Search ............ 210/198 C, 198.1, 198.2, 210/198.3; 422/70, 69; 73/61.1 C

[56] References Cited

U.S. PATENT DOCUMENTS 2,875,144  2/1959  Karler ............................ 204/299
3,623,841  11/1971 Kraffczyk et al. .................. 422/70

OTHER PUBLICATIONS

Whatman Prod. Bulletin 502, 2/1978.

Thin Layer Chromatography-A Lab. Handbook; E. Stahl, pp. 1-553; Cited 32, 33, 36, 37, 452-455, 395.

Primary Examiner—Michael S. Marcus
Attorney, Agent, or Firm—Lerner, David, Littenberg & Samuel

[57] ABSTRACT

A thin layer chromatography plate is disclosed for two-dimensional chromatography of a sample, in which the plate has a first surface portion including a first composition suitable to perform thin layer partition chromatography in a first direction on the plate and a second surface portion including a second composition suitable to perform thin layer chromatography in a second direction on the plate, wherein the second composition is selected from the group consisting of (1) a composition, different from the first composition, suitable to perform thin layer partition chromatography and (2) a composition suitable to perform adsorptive thin layer partition chromatography. A method of using such a plate is also disclosed.

2 Claims, 5 Drawing Figures

TWO DIMENSIONAL TWO PHASE THIN LAYER CHROMATOGRAPHY PLATE AND METHOD

BACKGROUND OF THE INVENTION

This invention relates to thin layer chromatography plates. More specifically, this invention relates to thin layer chromatography plates capable of performing two dimensional thin layer chromatography.

A number of thin layer chromatography plates which include more than a single layer on their surface are known. For example, U.S. Pat. No. 3,623,841 discloses a two layer plate for thin layer chromatography consisting of a first layer covering a minor portion of the plate which is of a composition suitable for separating amino acids from accompanying interfering substances (e.g., a strongly basic or strongly acidic polystyrene-based ion exchanger), and a second layer covering the remainder of the plate which is of a composition suitable to perform adsorptive thin layer chromatography of amino acids. The first layer of this patented plate does not perform any development of the amino acids along a first direction. Rather, this layer merely performs a washing operation to separate the amino acids from contaminants. The only development of the amino acids occurs in the second dimension, i.e., on the adsorptive layer.

U.S. Pat. No. 3,623,841 also mentions in its background section a prior thin layer chromatography plate suitable for two dimensional chromatography of fats and fatty acids. The plate is said to have a strip which is impregnated with silver nitrate. In the first dimension, the mixture is separated on the impregnated strip in accordance with the number and position of its double bonds. In the second dimension, a transition occurs from the impregnated strip to the non-impregnated layer where further separation of the mixture of substances is effected. The separation in the first dimension along the silver nitrate impregnated strip takes place by argentation thin layer chromatography.

The above prior art techniques have limited utility. For example, they do not provide for separation and determination of certain important materials, such as the separation of sulfonamides, separation of bile acids, and separation of pesticides and pharmaceuticals and their metabolites. A thin layer chromatography plate and method which could accomplish separation of such materials quickly, easily and accurately is accordingly very desirable.

SUMMARY OF THE INVENTION

It has now been found that such desirable characteristics are provided by a thin layer chromatography plate comprising a first surface portion including a first composition suitable to perform thin layer partition chromatography in a first direction on the plate, and a second surface portion including a second composition suitable to perform thin layer chromatography in a second direction on the plate, in which the second composition is selected from the group consisting of (1) a composition, different from said first composition, suitable to perform thin layer partition chromatography and (2) a composition suitable to perform adsorptive chromatography.

These thin layer chromatography plates have application in many areas of analysis and are suitable for quick, easy and accurate separation of many different types of materials such as sulfonamides, bile acids, pesticides, hydrocarbons such as from oil spills, and pharmaceuticals and their metabolites, e.g., librium and its metabolites. For example, using a combination of reverse phase partition thin layer chromatography and adsorptive thin layer chromatography compositions on the plate, the plates are particularly useful in the assay of animal meat to determine sulfonamides, which are additives to cattle feed. The present thin layer chromatography plate is also better than simple adsorptive thin layer chromatography plates in determining oil spill analysis. Moreover, using a composition suitable to perform reverse phase partition chromatography as one of the compositions on the plate, it is possible to separate a mixture of materials according to varying chain lengths of such materials, e.g., by the number of carbon atoms say in a series of bile acids or hydrocarbons.

In a preferred embodiment of the invention, one of the first and second surface portions of the plate comprises a minor portion of the plate and the other of the first and second surface portions comprises a major portion of the surface of the plate. In one such embodiment, one surface portion preferably comprises a strip along one edge of the plate with the remainder of the surface of the plate comprising the other surface portion.

The first and second compositions can be employed in all of the possible combinations of adsorptive chromatography, thin layer partition chromatography and reverse phase thin layer partition chromatography. In a preferred embodiment, one of the first and second compositions can comprise a composition suitable to perform reverse phase thin layer partition chromatography. In another preferred embodiment of the invention, the first surface portion of the plate includes a composition suitable to perform reverse phase thin layer partition chromatography and the second surface portion of the plate includes a composition suitable to perform thin layer partition chromatography. In another preferred embodiment, the first surface portion of the plate includes a composition suitable to perform reverse phase thin layer chromatography and the second portion of the plate includes a composition suitable to perform adsorptive thin layer chromatography.

Any of the compositions well known in the art for thin layer partition chromatography, reverse phase thin layer partition chromatography and adsorptive thin layer chromatography can be used in the present invention. Many such materials are discussed in "Thin Layer Chromatography" edited by Egon Stahl (2nd Ed., Springer-Verlag, New York, 1969). For example, suitable adsorptive thin layer chromatography compositions include silica gel, alumina, glass powder, calcium sulfate diatomaceous earth, phosphates and silicates such as magnesium silicate. Suitable materials for thin layer partition chromatography include cellulose, polyamide powder and silica gel with organic materials bonded to them, such as organic materials including hydrocarbon chains, polyaminocyano groups, polyamide groups, oxypropionitrile groups, ion exchange groups, and polyglycol or polyether groups. Suitable reverse phase thin layer partition chromatography compositions include silica gels having hydrophobic materials bonded to their surface, including aliphatic, aromatic and olefinic chains, such as hydrocarbon chains, e.g., octadecyl chains. One such composition suitable for reverse phase partition chromatography is the material known as $KC_{18}$ available from Whatman, Inc.

The thin layer chromatography plate of the present invention can be prepared by methods well-known in the art. In one method, the material suitable to perform the desired chromatography mode is mixed with a proper amount of a solvent, such as water or isopropanol, and, if desired, a binding agent, such as calcium sulfate or an appropriate polymeric material etc. A suitable phosphor can also be incorporated into the composition at this point, if desired. Such phosphors could include materials such as the zinc-cadmium compounds well-known in the art for this purpose. The viscosity of these mixtures is then adjusted so that the composition will properly coat a plate. This viscosity adjustment is done by various means conventional to the art, including adjusting the pH and mechanically stirring the mixture. The resulting slurries are loaded into a coating box which can be compartmented to keep the slurries of the two compositions (i.e., one for each of the first and second composition) separate. The slurries are applied to the plate at a proper thickness, usually by use of a coating machine, such as an automatic TLC coater model number 21602 made by Camag Inc.

The thickness of the coatings can vary depending upon the materials to be separated and the solvents used etc. Typically, the coating thickness is from about 100 to about 1000 microns and preferably from about 200 to about 250 microns. The plates after application of the first and second compositions are then dried. No special temperature or pressure conditions are required for making the plate of the present invention and ambient conditions are normally employed.

The size of the plate and the surface portions thereof vary depending upon the separation that is required. Typically, plates of from about 10 to about 20 cm in length are sufficient, but longer plates may be required for specific applications.

In accordance with the invention, there is also provided a process for chromatographically separating a mixture of materials in which a sample of said mixture is deposited on one end of a first surface portion of a thin layer chromatography plate, which first surface portion includes a first composition suitable to perform thin layer chromatography selected from adsorptive thin layer chromatography and thin layer partition chromatography. The thin layer chromatography plate also includes a second surface portion including a second composition, different from the first composition, suitable to perform thin layer chromatography selected from adsorptive thin layer chromatography and thin layer partition chromatography, with the proviso that, when the first composition is suitable to perform adsorptive thin layer chromatography, the second composition is suitable to perform thin layer partition chromatography. The thin layer chromatography plate is developed by placing the plate in contact with a first solvent such that the first solvent transports the mixture across the first portion of the plate for at least partially separating the mixture into its components parts by a first thin layer chromatography. After this first thin layer chromatography has taken place, the plate is removed from contact with said first solvent and dried. The plate is then further developed by placing the plate in contact with a second solvent, such that the second solvent transports the partially separated mixture from the first surface portion of the plate onto and across the second surface portion of the plate for further separating the mixture into its component parts by a second thin layer chromatography.

The thin layer chromatography plate of the present invention can be used in a manner similar to prior thin layer chromatography plates. Typically, the plate of the present invention with a sample spotted on the first surface portion of the plate is placed in a chamber containing the first solvent and a top is put on the chamber. The chamber can be saturated or non-saturated depending upon the material to be separated and the preference of the user. Typically, to obtain saturation, a piece of filter paper soaked with the appropriate solvent is placed in the chamber. The plate is placed in contact with the first solvent so that, when the solvent is transported across the plate, it at least partially separates the mixture forming the sample into its component parts along the first surface portion. The solvent is usually allowed to ascend the plate to a predetermined distance effective to achieve the desired separation, which distance varies depending on the materials used on the plate, the sample to be separated, and the solvents used, etc. Typically, the solvents are allowed to ascend to from about 10 to about 20 cm across the plate. The plate is then removed from the first solvent and dried to remove the first solvent. The plate is then placed in a chamber in contact with a second solvent such that, when the second solvent is transported across the plate, normally it transports the partially separated sample from the first surface portion onto and across the second surface portion so as to further separate the sample into its component parts. Normally, the first and second chromatographic developments are in directions perpendicular to each other. The separated mixture of the sample can than be analyzed by any of the well-known methods in the art. For example, visualization agents such as fluorescein, iodoplatinate, Dragondorff, Ninhydrin and phosphomolybdic acid can be used. Other suitable visualization agents are disclosed on pages 855-905 of the Stahl reference cited above.

During the process of the invention, the thin layer chromatography plate can be subjected to the normal procedures of thin layer chromatography. For example, if one of the first and second surface portions includes a composition suitable for adsorptive thin layer chromatography, the plate is activated by heating it at an elevated temperature, for example, by heating from about 110° C. to about 120° C. for about 10 to about 15 minutes. Typically, such a plate can be activated by heating at about 110° C. for about 10 minutes. Also, in cases where adsorptive chromatography is the second mode of thin layer chromatography to be performed by the plate, the plate should be reactivated by heating before contacting with the second solvent and substantially all of the first solvent should be removed from the plate. These techniques can, of course, be varied in many respects depending upon the knowledge and preference of the user.

The solvents used in the method of the present invention include any of the solvents well-known in the art to be useful for performing the desired separation step, i.e., for adsorptive chromatography, thin layer partition chromatography or reverse phase thin layer partition chromatography. For example, suitable solvents for use in performing thin layer partition chromatography and reverse phase thin layer partition chromatography include polar solvents, such as acetonitrile/water mixtures and alcohol/water mixtures. For adsorptive thin layer chromatography, suitable solvents include aromatic hydrocarbons, ketones, chlorinated hydrocarbons, and alcohols, such as toluene, chloroform, and acetone.

DETAILED DESCRIPTION OF THE INVENTION

Figure 1:
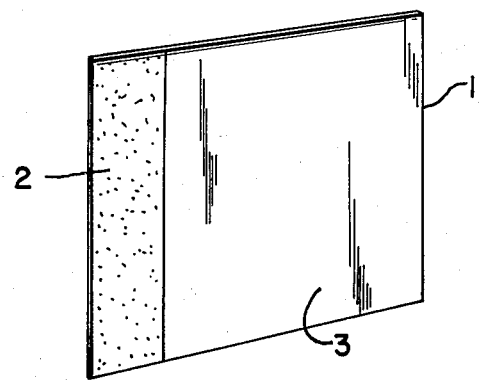
FIG. 1 shows a perspective view of a thin layer chromatography plate in accordance with one embodiment of the present invention.

The thin layer chromatography plate of the present invention is best described with reference to FIG. 1 which shows an embodiment of the invention in which the thin layer chromatography plate 1 contains a strip 2 covering a minor portion of the plate. The first surface portion or strip 2 can be composed of a first composition suitable to perform thin layer partition chromatography or adsorptive thin layer partition chromatography. For purposes of example, the first composition can be silica gel so that the first surface portion is suitable to perform adsorptive thin layer chromatography. The remainder of the plate 2 is covered by a second surface portion or layer 3 which is composed of a second composition, different from the first composition, suitable to perform thin layer partition chromatography or adsorptive thin layer chromatography. Again, for purposes of example, the second composition can be silica gel having a hydrophobic group attached to the surface, such as octadecyl groups (KC$_{18}$ as sold by Whatman Inc.) so that the second surface portion of the plate is suitable to perform reverse phase partition chromatography.

Figure 2:
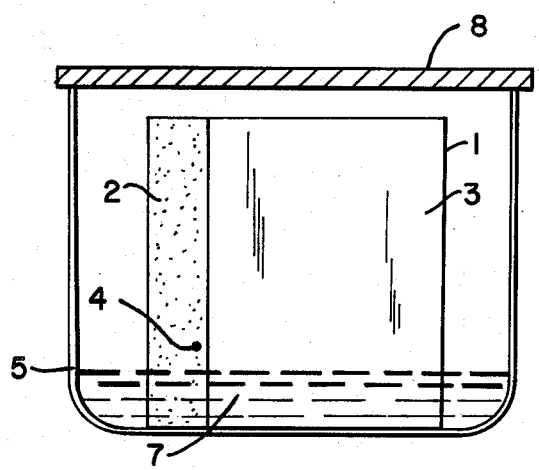
FIG. 2 shows a cross-sectional view of a developing chamber containing a thin layer chromatography plate in accordance with one embodiment of the present invention.
Figure 3:
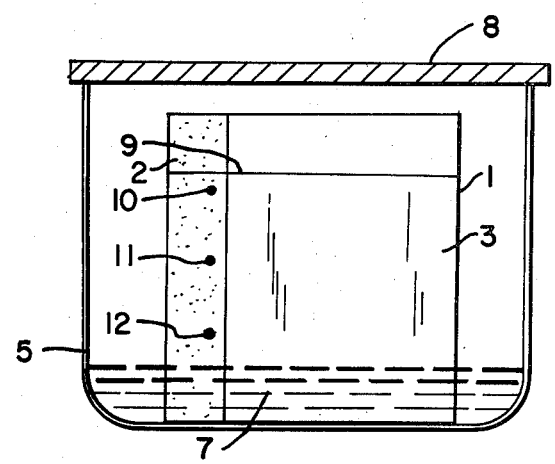
FIG. 3 shows a cross-sectional view of a developing chamber containing a thin layer chromatography plate in accordance with the present invention after partial development has taken place along one of the surface portions of the plate.

The use of the thin layer chromatography plate of the present invention is best illustrated by the sequence of FIGS. 2-5. Thus, normally the plate is first activated by heating it in an oven. The sample 4 containing a mixture of materials to be separated is spotted on one end of the strip 2. This spot 4 is then dried, e.g., by a current of warm air from a heat gun. The plate 1 is then placed in a conventional developing chamber 5 containing the first solvent 7. If desired, a trough could be placed in the chamber 5 to hold the solvents. The plate 1 is placed in the chamber 5 so that the first solvent 7 will ascend the plate along the longitudinal direction of the strip 2 as is illustrated in FIG. 2. A cover or top 8 is usually placed on the developing chamber. The developing chamber can be saturated or non-saturated with the first solvent, as desired by the operator. As the first solvent 7 ascends the plate 1 as shown by solvent line 9 in FIG. 3, the sample 4 is at least partially separated into its components as shown by members 10, 11 and 12 of FIG. 3. Thus, FIG. 3 illustrates the process of the present invention at the point at which the sample is partially developed along the strip 2.

Figure 4:
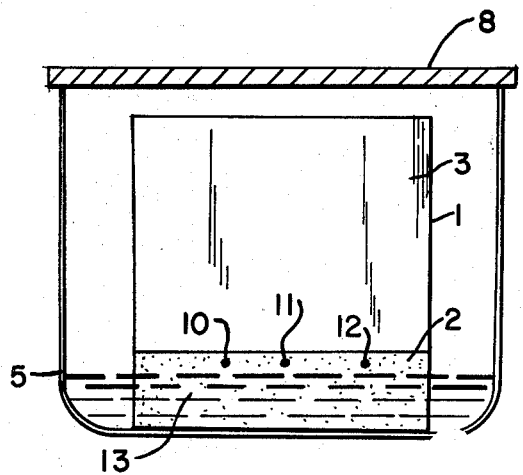
FIG. 4 shows a cross-sectional view of a developing chamber containing a thin layer chromatography plate in accordance with the present invention in which the plate is in position for development on the second surface portion of the plate.
Figure 5:
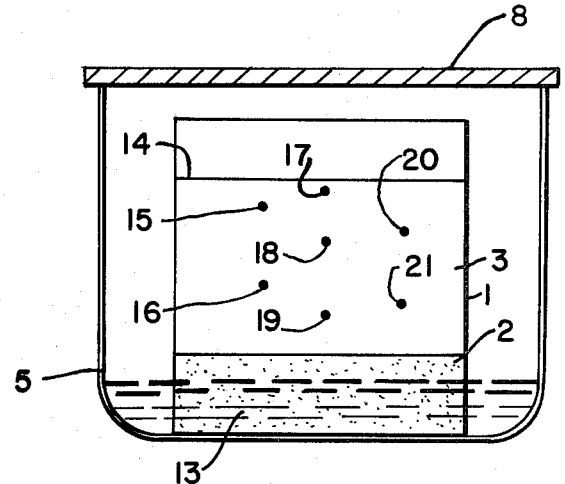
FIG. 5 shows a cross-sectional view of a developing chamber containing a thin layer chromatography plate in accordance with the present invention in which development of the sample has taken place on the second surface portion of the plate.

The plate is then removed from the developing chamber 5 and, if desired, is dried in an oven and allowed to cool to an appropriate temperature, normally room temperature. Again, the chamber during the separation step can be saturated or non-saturated as desired by the operator. The plate is then returned to the developing chamber and placed in contact with a second solvent 13 as shown in FIG. 4 so that, as the solvent 13 ascends the plate to solvent line 14 as shown in FIG. 5, it transports the partially separated sample (i.e., members 10, 11 and 12) from strip 2 onto and across the second surface portion 3 to further separate the sample 4 into its component parts, as is illustrated by members 15, 16, 17, 18, 19, 20 and 21 in FIG. 5. The plate can then be removed from the developing chamber and dried again. The separated components can be analyzed and/or visualized by conventional techniques, e.g., by spraying with reagents such as fluorescamine and then observing the spots under a fluorescent light.

The following examples are presented for the purposes of illustrating, but not limiting, the apparatus and process of the present invention.

EXAMPLE 1

A thin layer chromatography plate 20 centimeters by 20 centimeters was prepared having a 3 centimeter by 20 centimeter strip of KC$_{18}$ (which is a silica gel having attached to the surface thereof octadecyl hydrocarbon groups sold by Whatman, Inc.) with the remainder of the plate being covered with a standard silica formulation (K$_5$ having 80A pore size manufactured by Whatman, Inc.). Both layers were applied as 200 micron coatings on flat glass of about 1 mm thickness.

The plate was activated in an oven at 110° C. for ten minutes. A sample containing a mixture of the following thirteen sulfonamides at a concentration of 1 mg/ml in acetone:methanol (9:1 by volume) was prepared:

Sulfadiazine
Sulfamethazine
Sulfamenazine
Sulfathiazole
Sulfaquinoxaline
Sulfabromethazine
Sulfaethoxypyridazine
Sulfadimethoxine
Sulfachlorpyridazine
Sulfanilamide
Sulfapyridine
Sulfaguanidine
Sulfisoxazole A sample of 5 ul was spotted on one end of the KC$_{18}$ layer 1.5 centimeters from the side of the plate. This spot was dried under a current of warm air from a heat gun.

100 ml of a solvent mixture containing 80 percent toluene and 20 percent methyl cyanide was poured into a developing chamber containing a piece of Whatman saturation paper. The top as placed on the chamber and left to equilibrate for fifteen minutes. The spotted plate was then placed in the chamber so that the sample spot was just above the solvent and solvent was allowed to ascent to 16 centimeters from the point of application of the sample. This ascension or development took approximately 37±4 minutes. The plate was removed from the chamber, dried in an oven at 110° C. for fifteen minutes and allowed to cool to room temperature.

A solvent mixture containing 85 ml ethylacetate, 15 ml methanol and 0.6 ml ammonium hydroxide was poured into a developing chamber which did not contain saturation paper. The plate was immediately placed in the developing chamber so that the solvent mixture would ascend from the strip of $KC_{18}$ onto and along the adsorptive layer of silica and the top placed on the chamber. The solvent mixture was allowed to ascend to 14 centimeters from the point of attachment. This took approximately 53±minutes. The plate was then removed from the chamber and dried in an oven at 110° C. for fifteen minutes.

The plate was sprayed heavily yet uniformly with fluorescamine reagent (Whatman KSR-F) to allow visualization of the separated compounds. The spots were then observed fluorescing under 366 nm light (long wave).

Several duplicate runs by the above procedure indicated a high degree of reproducibility. In each case, the thirteen compounds were separated sufficiently to identify each. These results demonstrate that the thin layer chromatography plate and method of the present invention can advantageously be used to separate sulfonamides quickly, easily and accurately.

EXAMPLE 2

A thin layer chromatography plate, as described in Example 1, is washed overnight in a tank containing chloroform:methanol (1:1). The plate was then dried.

A sample containing 5 ul of human bile diluted 1:100 was prepared. A mixture of standards was also prepared by mixing the following: glycocholic acid (GC), taurocholic acid (TC), glycodeoxycholic acid (GDC), taurodeoxycholic acid (TDC), glycochenodeoxycholic acid (GCDC) and taurochenodeoxycholic acid (TCDC). The bile sample was applied to the starting point of the KC 18 strip. On another such plate, a sample of the mixture of standards was applied in a similar manner. Development of both plates are separately performed to the top of the plate along the KC 18 strip using as the mobile phase ehtanol: 0.01 M $KH_2PO_4$ (pH 2.5) (1:1).

After thorough drying, each plate is turned 90° and development is performed separately for each plate along the silica portion of the plate with chloroform, methanol, acetic acid, water (75:25:5:5) as mobile phase. After development is completed, the plates are dried in the air and then dried for four minutes in an oven at 170° C., in order to completely remove the solvent. The plates are then separately sprayed lightly with a solution of 10 percent $H_2SO_4$ in ethanol. After drying in air, the plates are heated in an oven for five minutes at 170° C. in order to develop fluorescence of the bile acids. Overheating will result in charring of the layer and should thus be avoided. After cooling, the plates may be viewed under ultraviolet light and clear separation of all six bile acids will be seen. These results demonstrate that conjugated bile acids can be separated by employing the apparatus and method of the present invention. Previous thin layer chromatography methods gave only partial separation of the conjugated bile acids.

It will be understood that the embodiments described above are merely exemplary and that persons skilled in the art may make many variations and modifications without departing from the spirit and scope of the invention. All such modifications and variations are intended to be included within the scope of the invention as defined by the appended claims.

What is claimed is:

1. A thin layer chromatography plate for two-dimensional chromatography of a sample, said plate comprising a first surface portion consisting essentially of silica gel having octadecyl groups attached thereto, said first composition being suitable to perform reverse phase thin layer partition chromatography in a first direction on said plate, and a second surface portion including a second composition, different from said first composition, comprising silica gel, said second composition being suitable to perform adsorptive chromatography in a second direction on said plate.

2. A thin layer chromatography plate according to claim 1, wherein said first surface portion is a strip along one side of said thin layer chromatography plate.

* * * * *